United States Patent
Krumbholz et al.

(10) Patent No.: US 9,470,667 B2
(45) Date of Patent: Oct. 18, 2016

(54) APPARATUS FOR DETERMINING AND/OR MONITORING AT LEAST ONE PROCESS VARIABLE

(75) Inventors: Andreas Krumbholz, Maulburg (DE); Volker Dreyer, Lorrach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 213 days.

(21) Appl. No.: 14/353,597

(22) PCT Filed: Sep. 12, 2012

(86) PCT No.: PCT/EP2012/067828
§ 371 (c)(1),
(2), (4) Date: Apr. 23, 2014

(87) PCT Pub. No.: WO2013/060521
PCT Pub. Date: May 2, 2013

(65) Prior Publication Data
US 2014/0260709 A1    Sep. 18, 2014

(30) Foreign Application Priority Data
Oct. 24, 2011  (DE) .......................... 10 2011 085 128

(51) Int. Cl.
*G01N 33/00*  (2006.01)
*G01D 11/24*  (2006.01)
(Continued)

(52) U.S. Cl.
CPC .............. *G01N 33/00* (2013.01); *G01D 11/245* (2013.01); *G01F 23/00* (2013.01); *G01F 23/2961* (2013.01); *G01F 23/2965* (2013.01); *G01F 23/2967* (2013.01)

(58) Field of Classification Search
CPC .... G01D 11/245; G01D 11/30; G01F 23/00; G01F 23/242
See application file for complete search history.

(56) References Cited

U.S. PATENT DOCUMENTS

| 5,866,815 A | 2/1999 | Schwald et al. |
| 6,352,361 B1 * | 3/2002 | Nimberger ............. G01K 13/02 |
| | | 374/142 |

FOREIGN PATENT DOCUMENTS

| DE | 3623741 A1 | 1/1988 |
| DE | 4311963 A1 | 10/1994 |

(Continued)

OTHER PUBLICATIONS

Machine translation of: DE3623741 (Jan. 28, 1988) provided by Applicants.*

(Continued)

*Primary Examiner* — Daniel S Larkin
*Assistant Examiner* — Jamar Ray
(74) *Attorney, Agent, or Firm* — Bacon & Thomas, PLLC (57) ABSTRACT

An apparatus for determining and/or monitoring at least one process variable of a medium, comprising at least one sensor element sensitive for the process variable, a process connection for securing the apparatus to a container or pipeline and a housing connected with the process connection. The apparatus has at least one, first component of metal and at least one, second component of synthetic material, wherein the first component and the second component are embodied as hollow bodies. An annular, first connection region is formed on the first component, wherein on the second component an annular second connection region is formed, whose outer diameter corresponds at least sectionally to the inner diameter of the first connection region. The second connection region is introduced into the first connection region, and a securement structure is present, which is dimensioned and positioned in such a manner that the securement structure presses the second connection region at least sectionally against the first connection region.

9 Claims, 5 Drawing Sheets

(51) Int. Cl.
*G01F 23/296* (2006.01)
*G01F 23/00* (2006.01)

(56) References Cited

FOREIGN PATENT DOCUMENTS

| DE | 102009039633 | A1 | 3/2011 |
|---|---|---|---|
| EP | 0660482 | A1 | 6/1995 |
| EP | 0984248 | A1 | 3/2000 |
| EP | 2136192 | A1 | 12/2009 |
| WO | 2013060521 | A1 | 5/2013 |

OTHER PUBLICATIONS

Dec. 19, 2012 International Search Report, EPO, The Netherlands.
English Translation of the International Preliminary Report on Patentability, WIPO, Geneva, May 8, 2014.

* cited by examiner

APPARATUS FOR DETERMINING AND/OR MONITORING AT LEAST ONE PROCESS VARIABLE

TECHNICAL FIELD

The present invention relates to an apparatus for determining and/or monitoring at least one process variable of a medium in a container or a pipeline. The apparatus includes at least one sensor element sensitive for the process variable, a process connection for securing the apparatus to the container or the pipeline and a housing for residing outside of the container or pipeline, which housing is connected with the process connection. For example, the sensor element is a probe for capacitive and/or conductive, fill level measurement, or a rod or an oscillatory fork for vibronic, fill level measurement. The invention is, however, not limited to certain process variables or sensor elements.

BACKGROUND DISCUSSION

Container, or pipeline, wall mountable measuring devices utilize, in general, a process connection, which is connected, on the one hand, with a sensor element and, on the other hand, with a housing. The sensor element is mountable via the process connection in such a manner to the container or pipeline that it protrudes inwardly into the interior of the container or pipeline or at least faces the interior. The housing remains outside of the container or pipeline and accommodates, as a rule, electronic components of the measuring device. In order to prevent damage to these electronic components, a fixed and sealed connection of housing and process connection is required.

The process connection is, as a rule, made of metal. A housing, likewise of metal, is, for example, weldable with the process connection. When a housing is made of synthetic material, e.g. plastic, this kind of joining technology is not feasible. A first option is to provide a screw thread on each of two parts to be connected together and then screw them together. Known from Offenlegungsschrift (German Laid Open Application) EP 0660482 A1, for example, is a pressure sensor having a cylindrical housing, into which a housing lid is screwed. Providing process connection and housing each with a screw thread is, however, relatively complicated, the more so, since, for twist resistance, an adhesive is supplementally required.

Another connection option involves introducing a neck shaped section of one of the parts into the other part and to secure the assembly by means of a snap ring. This connection is, however, not shape-interlocked and additionally not secured against twisting of one part relative to the other part.

SUMMARY OF THE INVENTION

An object of the invention is to provide an apparatus for determining and/or monitoring at least one process variable, which apparatus has a secure and simply manufactured connection between a first component of metal and a second component of synthetic material.

The object is achieved by an apparatus for determining and/or monitoring at least one process variable of a medium in a container or a pipeline, comprising at least one sensor element sensitive for the process variable, a process connection for securing the apparatus to the container or pipeline and a housing for residing outside of the container or pipeline, which housing is connected with the process connection, wherein the, apparatus has at least one, first component of metal and at least one, second component of synthetic material, wherein the first component and the second component are embodied as hollow bodies, wherein an annular first connection region is formed on the first component, wherein on the second component an annular second connection region is formed, whose outer diameter corresponds at least sectionally essentially to the inner diameter of the first connection region, wherein the second connection region is introduced into the first connection region, and wherein a securement means is present, which is dimensioned and positioned in such a manner that the securement means presses the second connection region at least sectionally against the first connection region.

In a first embodiment of the solution of the invention, the first connection region includes at least one cavity. The cavity is an indentation or channel in the first connection region. The cavity is preferably introduced peripherally into the first connection region, for example, in the form of a groove. The second connection region engages in the cavity. The cavity prevents withdrawal of the second connection region from the first component.

In an embodiment of the apparatus, the second connection region has at least one detent, which engages in the cavity. The detent is, for example, a projection. The second connection region is embodied in such a manner that it possesses a spring action, so that the second connection region is introducible into the first connection region and the at least one detent can engage in the cavity. The spring action is achieved, for example, by introducing slots into the second connection region, so that tongues form, which can be pressed together for the introduction of the second connection region into the first connection region.

In an alternative embodiment of the apparatus, the shape of the second connection region is matched in such a manner to the cavity that the second connection region, pressed by the securement means into the cavity, and the first connection region enter into a shape interlocking connection. In the simplest case, the inner wall of the first connection region is inclined by the cavity. The outer wall of the second connection region is correspondingly likewise inclined, wherein the inclination is opposite to the inclination in the first connection region in such a manner that the securement means of the second connection region presses into the cavity and the inner wall of the first connection region and the outer wall of the second connection region contact one another. Also, in this embodiment, the second connection region can have a slotting, in order to achieve a spring action.

In an embodiment, the first component is the process connection and the second component is the housing or a part of the housing, or the first component is a first part of the housing and the second component is a second part of the housing. The process connection of an apparatus of the field of the invention is, as a rule, manufactured of stainless steel. A housing of synthetic material is connectable with the process connection. There are, however, also housings known, which are likewise of metal, especially aluminum, and, for example, welded with the process connection. Such housings can have, for example, a lid of synthetic material. The connection of the invention between metal component and synthetic material component can, consequently, not only be between a metal process connection and a housing of synthetic material, but, instead, for example, also between a metal housing body and a lid of synthetic material.

In an embodiment, the contour of the securement means is matched sectionally to the second component. The securement means comprises, in such case, one, a section, which exerts a radial force on the second connection region and thereby assures the fixed connection between first and second components, and two, a projection, which represents a kind of insert for the second component and serves to reinforce the wall of the second component. This embodiment is especially advantageous in the case of an essentially tubular, second component.

In an embodiment, the securement means or the second component includes at least one locking element, which affixes the securement means in the axial direction. The locking element is, for example, a detent, which engages in a corresponding counterpart in the oppositely lying component, i.e. the second component or the securement means. The locking element can also be a snap-in part on the second component, which is arranged above the securement means and prevents this from slipping out of position.

An embodiment provides that the second component has a groove, and that a retaining ring is introduced into the groove to affix the securement means in the axial direction.

In an embodiment, at least one sealing means is provided between the first connection region and the second connection region. The sealing means is, for example, an O-ring. The sealing means seals a possibly existing gap between the first and second components, so that a penetration of moisture or dirt into a hollow space between the two components is prevented. This is especially of advantage when such a hollow space serves for accommodating electronic components.

An embodiment provides that the first component and the second component have essentially the same outer diameter, at least in a connecting section between the first component and second component. The outer walls of the first and second components lie preferably aligned with one another. The connecting section between the first and second components is thereby outwardly gap-free, so that a penetration of moisture and dirt into the inner space formed by the first and second components is prevented or at least made difficult.

The apparatus of the invention exhibits a shape interlocking, and force interlocking, connection between the first and second components. The connection can be effected in simple manner, since the two components need only be plugged together and the securement means pressed in. The complex introduction of threads for a threaded engagement is no longer required. Likewise absent are adhesives and welding. The synthetic material component can be produced as an injection molded part. This holds also for the securement means, wherein the securement means can alternatively also be embodied in metal. Through suitable providing of the cavity and/or a locking means, the connection is not only stable in the axial direction, but, also, additionally secured against twisting. An undesired releasing of the connection is not possible.

BRIEF DESCRIPTION OF THE DRAWINGS

The invention will now be explained in greater detail based on the appended drawing, the figures of which show respectively advantageous embodiments. The invention is not limited to the illustrated embodiments. The figures are, in each case, schematic representations. The figures of the drawing show as follows.

DETAILED DISCUSSION IN CONJUNCTION WITH THE DRAWINGS

Figure 1:
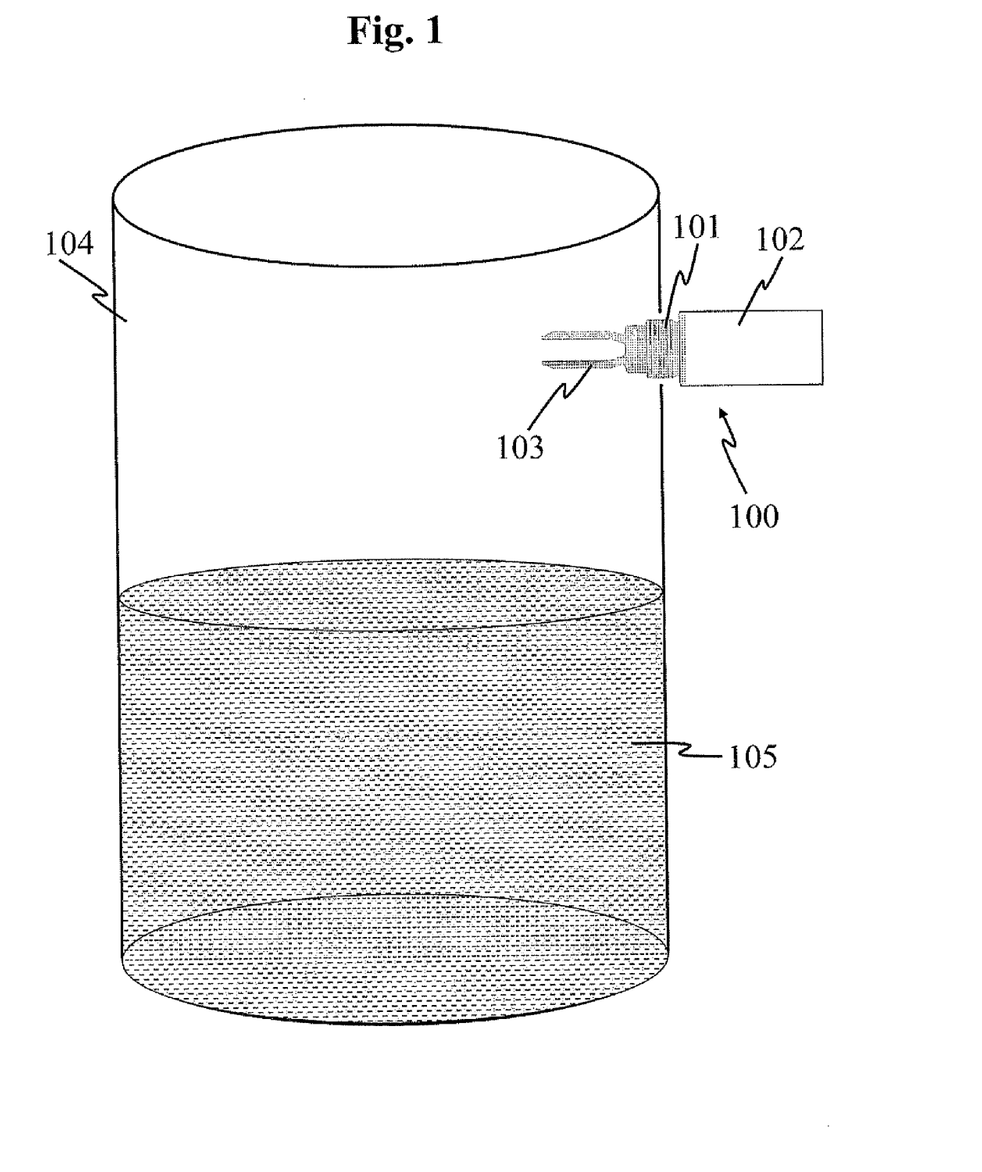
FIG. 1 is an apparatus for fill level measurement.

FIG. 1 shows an apparatus, in the following referred to as measuring device 100, for monitoring a limit level and for determining the density or the viscosity of a medium 105 in a container 104. Measuring device 100 includes a cylindrical, tubular housing 102, which is connected with a likewise tubular, process connection 101. Process connection 101, in turn, is connected with a sensor element 103 comprising two paddles carried on a membrane. Via the process connection 101, the measuring device 100 is securable in the wall of a container 104, so that the sensor element 103 protrudes inwardly into the container. For this, the process connection 101 includes an external thread. There are, however, also other embodiments of process connections 101, for example, process connections utilizing a flange connection.

While the process connection 101 is metal, housing 102 in this form of embodiment is a part formed of synthetic material, e.g. a plastic. Measuring devices 100 with housings of synthetic material are frequently utilized as cost effective alternatives to measuring devices 100 with metal housings and are generally applicable, where no special requirements are placed on the housing based on safety specifications, for example, in explosion protected regions,. The connection between process connection 101 and housing 102 must be stable and not come undone.

The connecting mechanism between housing 102 and process connection 101 of a measuring device 100 of the invention will now be explained in greater detail with reference to the following figures. The invention is, however, not limited to vibronic, fill level measuring devices.

Figure 2:
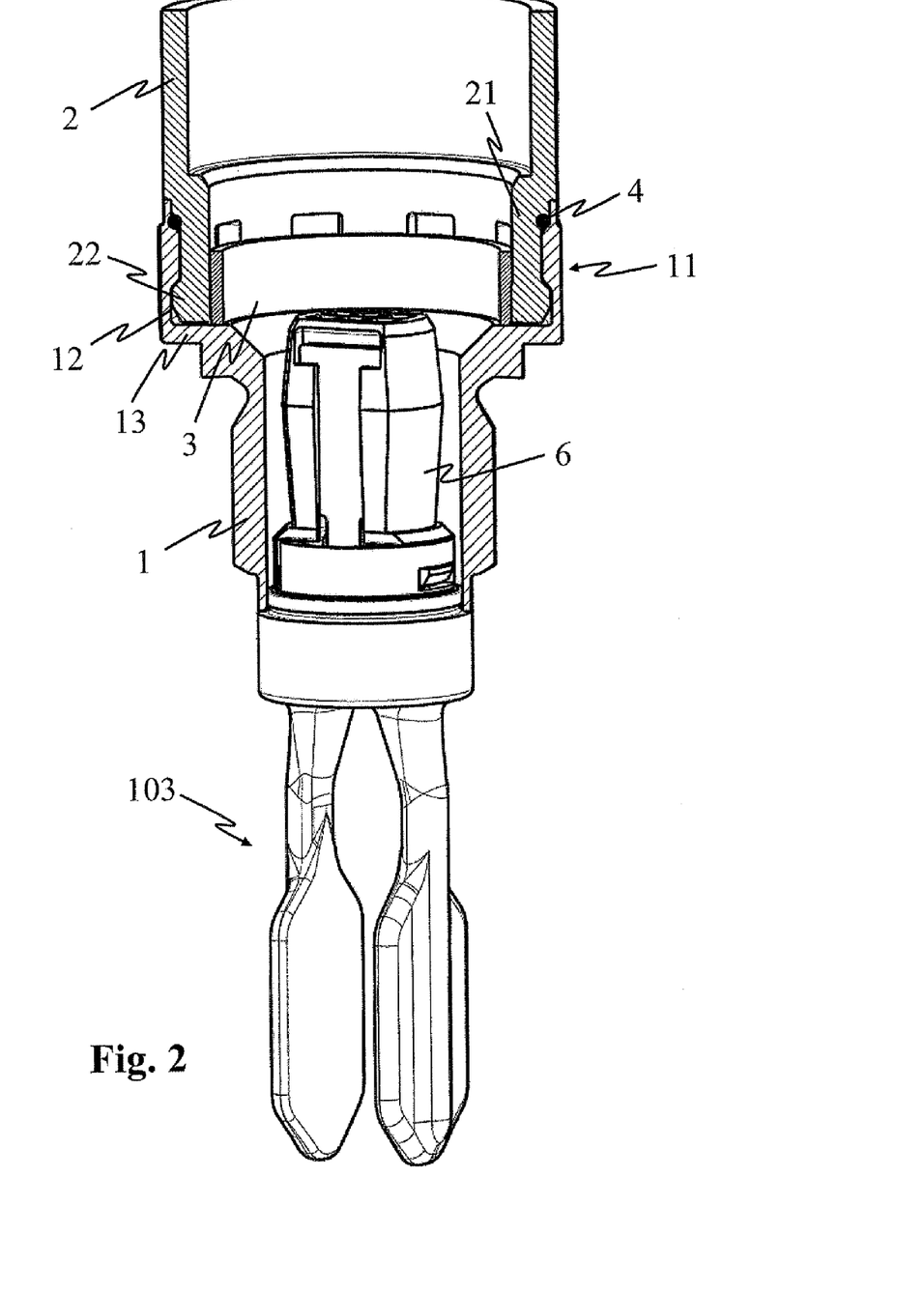
FIG. 2 is a first form of embodiment of the joint between process connection and housing.

FIG. 2 discloses a schematic, sectional illustration of a detail of a measuring device 100. The section includes the process connection 101 and a part of the housing 102. The sensor element 103 follows in the lower region of the figure and is indicated only schematically. In this example of an embodiment, the process connection 101 forms the metal, first component 1 and the housing 102 the plastic, second component 2 of the measuring device 100.

The first component 1 includes a tubular section, in whose outer wall, for example, a threaded section is provided. The tubular section serves, among others, to accommodate a connection plug 6 for electrical contacting of the sensor element 103. The tubular section transitions into an annular, first connection region 11. The diameter of the annular connection region 11 exceeds that of the tubular section, wherein the transitional region is embodied as a shoulder 13. Shoulder 13 forms a bearing surface for the second connection region 21 of the second component 2. Alternatively, the first component 1 can also have an essentially constant diameter, wherein then a necking is provided, which divides the first connection region 11 from the remaining part of the first component 1 and provides the bearing surface. Provided in the first connection region 11 is a cavity 12 in the form of a channel.

The second component 2 includes a tubular section and a second connection region 21 and is introduced into the first component 1 in such a manner that the first connection region and the second connection region 21 overlap. In the assembling, the second component 2 is introduced into the first component 1 in such a manner that the second connection region 21 and the first connection region 11 overlap. The second connection region 21 points, in such case, in the direction of the shoulder 13 of the first connection region 11, without lying on such. The tubular section of the second component 2, in contrast, strikes an outer edge of the first connection region 11. In this way, a bearing stop is formed. The outer diameters of the first connection region 11 and of the second connection region 21 are essentially equal, so that a shape interlocking connection is formed and a gap-free, common, outer surface is formed. In this way, a penetration of moisture into the hollow space defined by the first component 1 and second component 2 is prevented. The sealing action is further reinforces by a sealing ring 4, which is introduced as sealing means between the first connection region 11 and the second connection region 21. First connection region 11 and/or second connection region 21 can utilize a groove for accommodating the sealing ring 4 or be so formed that a gap for accommodating the sealing ring 4 is provided.

The second connection region 21 is formed in this embodiment as a snap-in part on the second component 2 and includes a plurality of detents 22, which are located on tongues isolated from one another by slots. There are at least two tongues with detents 22, preferably four to ten, especially eight. The slots reduce the stiffness of the second connection region 21 compared with the remaining part of the second component 2 and make the second connection region 21 capable of snapping into the first connection region 11. The detents 22 engage in the cavity 12 in the first connection region 11. In this way, the second connection region 21 becomes fixed in the axial direction in the first connection region 11.

In order to assure a fixed engagement of the detents 22 in the cavity 12 and to prevent a slipping of the detents 22 out of the cavity 12, a securement means 3 is provided, which exerts a force in the radial direction outwardly on the tongues bearing the detents 22. Securement means 3 is in the assembling pushed from above into the second component 2 and is pressed in the direction of the first component 1, for example, by means of a piston-like plug, until stopping on the shoulder 13. Positioned there, the securement means 3 presses the detents 22 into the cavity 12 and provides, thus, a force, and shape, interlocking connection between the first component 1 and the second component 2.

In a variant, securement means 3 is a separate component. In this case, the securement means 3 can be produced from the same material as the second component 2 or from another material, for example, from a stronger plastic or from a metal. In another variant, the securement means 3 and the second component 2 are formed as a single injection molded part, wherein the securement means 3 is connected via a thin web with the tubular section of the second component 2. In the assembling, the piston-like plug of the mounting tool pressing in the direction of the first component 1 ruptures the web and moves the securement means 3 into position. This embodiment enables an especially simple and cost effective manufacture.

Securement means 3 is ring-shaped in the simplest case. The height of the securement means 3 corresponds, in such case, at least to the height of the cavity 12, so that a pressing in of the detents 22 is assured. For an increased stability, the securement means 3 can also be taller. For example, its height can correspond to the height of the second connection region 21. In an embodiment, the securement means 3 has a projection, which is matched in its contour to the shape of the second component 2, so that the securement means 3 lies tightly against the second component 2. The projection acts as reinforcing on the wall presented by the second component 2 and effects a greater stability of the second component 2.

Preferably embodied on the projection is a detent, which engages in a groove introduced at corresponding height in the second component 2 and so affixes the securement means 3 in the axial direction. Such a detent can equally be provided on an annular securement means 3 not having the projection. Other locking options are presented in FIGS. 2a and 2b.

Through the engagement of the second connection region 21 in the cavity 12 and the securement means 3, in given cases, supplementally locked in the axial direction, the second component 2 becomes solidly connected with the first component 1. A rotation of the second component 2 in the first component 1 remains, however, possible. In order to suppress such a rotation, it is advantageous to provide the second connection region 21 or the first connection region 11 with at least one rotation preventing element (not shown). Preferably, two such twist preventing elements are provided. The twist preventing element is composed, for example, of a lug embodied on one of the two components, and the corresponding counterpart on the respectively other component to serve for receiving the lug. For example, two of the detents 22 have each a recess and the cavity 12 includes two projecting lugs. The lugs engage in the recesses in the detents 22 and thereby affix the second connection region 21 to the first connection region 11. Such a twist prevention is advantageous, for example, in order to prevent a twisting of contact wires or flexible circuit boards, which connect the connection plug 6 with an electronics unit provided in the second component 2. The twist protection elements represent, moreover, a positioning aid in the case of assembling the second component 2 with the first component 1.

In an embodiment, the inner wall of the second component 2 has at least one guide rail for a circuit board. The circuit board has a socket for receiving the contacts of the connection plug 6, or contacts for introduction into the connection plug 6. The same holds also for the forms of embodiment illustrated in the following figures.

Figure 2A:
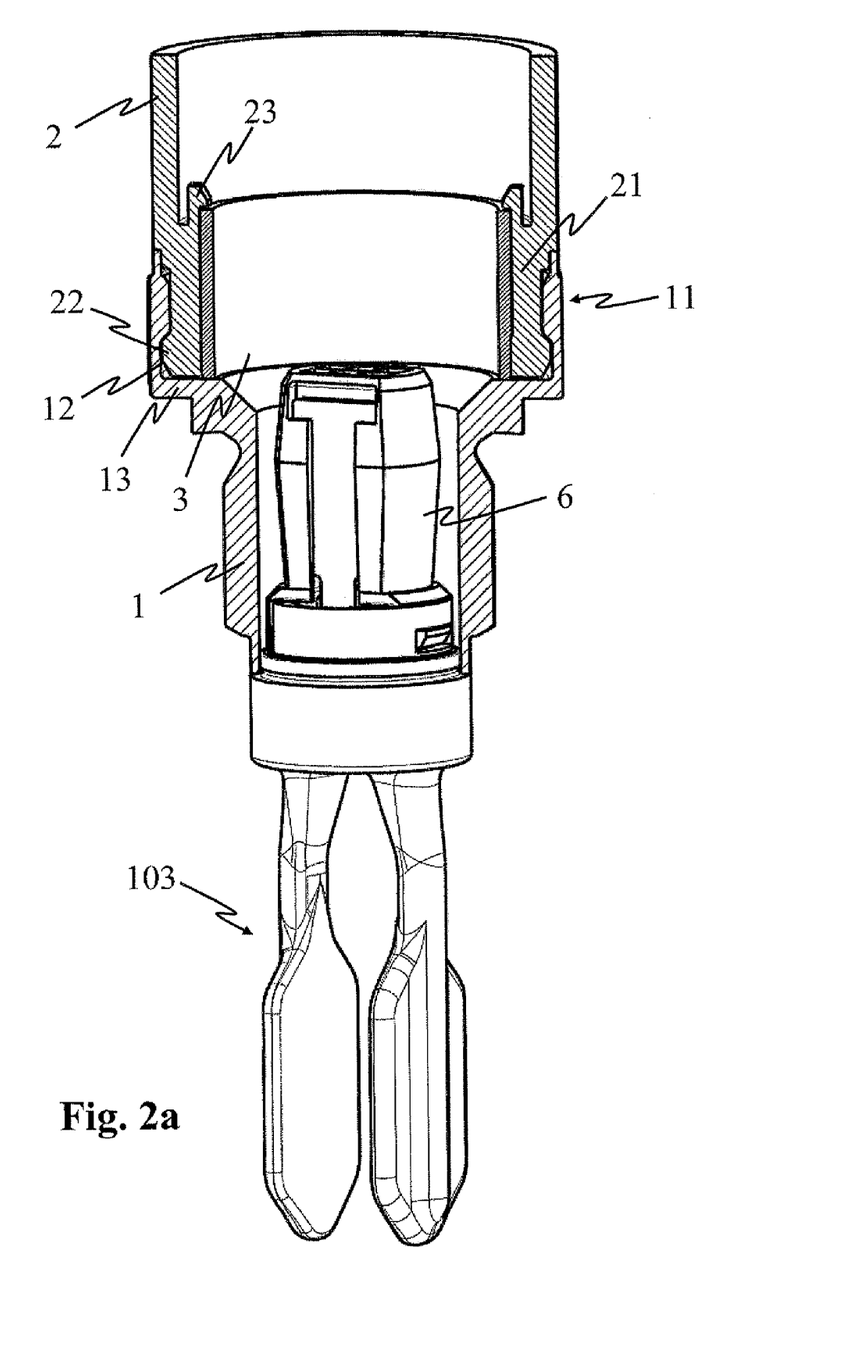
FIG. 2a is a first variant of the apparatus of FIG. 2.

FIG. 2a illustrates a first variant for affixing the securement means 3, whereby a releasing and shifting of the securement means 3 in the axial direction is prevented. For this, two locking elements 23 are embodied on the second component 2. The height of the securement means 3 corresponds to the height of the second connection region 21. The locking elements 23 are embodied as hook shaped, snap-in parts, which are arranged in such a manner that they lie on the upper edge of the securement means 3. Through their embodiment as snap-in parts, the locking elements 23 provide no insuperable mechanical resistance in the assembling of the securement means 3.

Figure 2B:
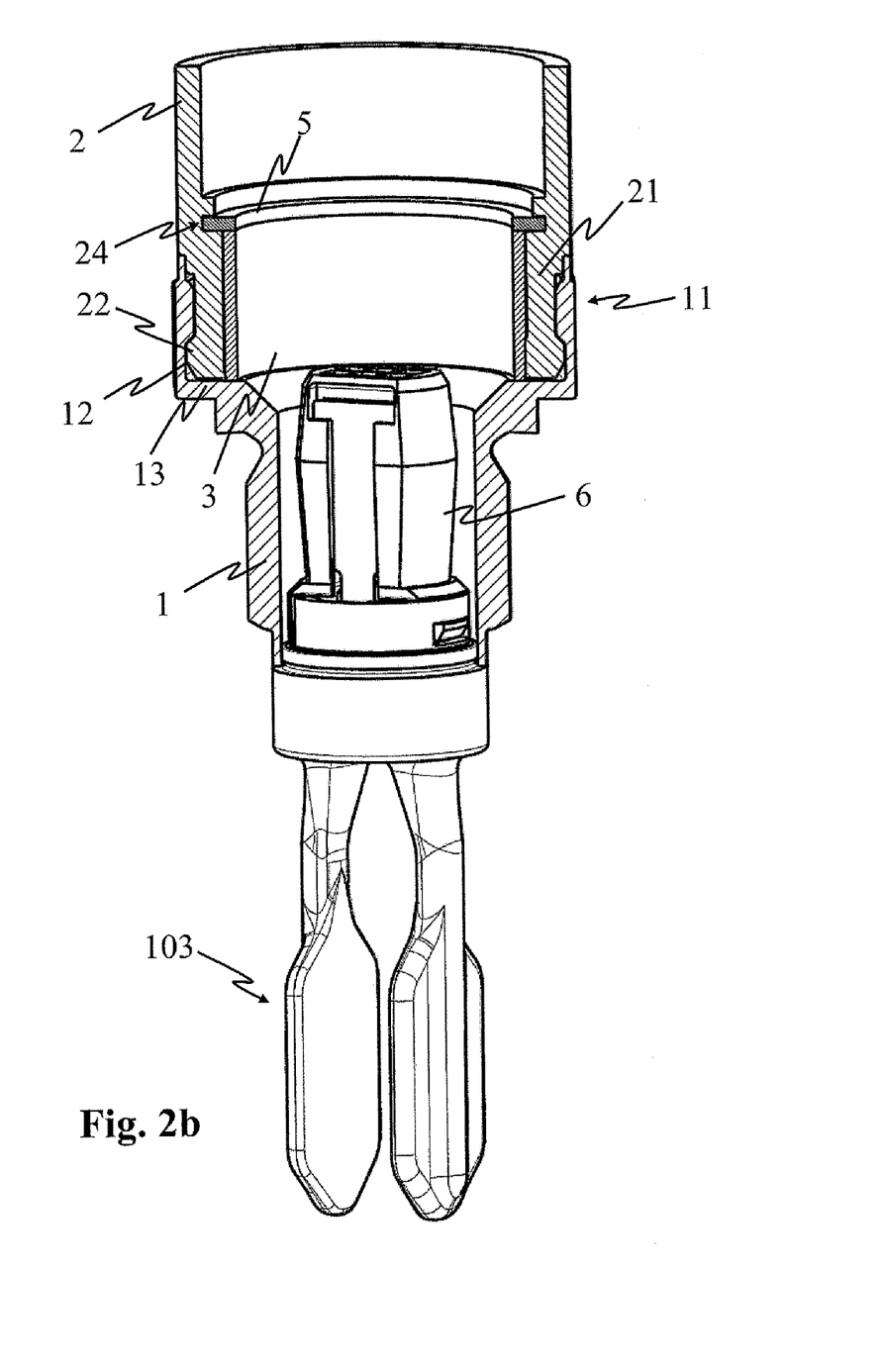
FIG. 2b is a second variant of the apparatus of FIG. 2.

FIG. 2b shows a second variant for securing the securement means 3 in the axial direction. The affixing of the securement means 3 is implemented by a retaining ring 5 embodied as a separate component or as part of the securement means 3. The retaining ring 5 engages in a groove 24 in the second component 2.

Figure 3:
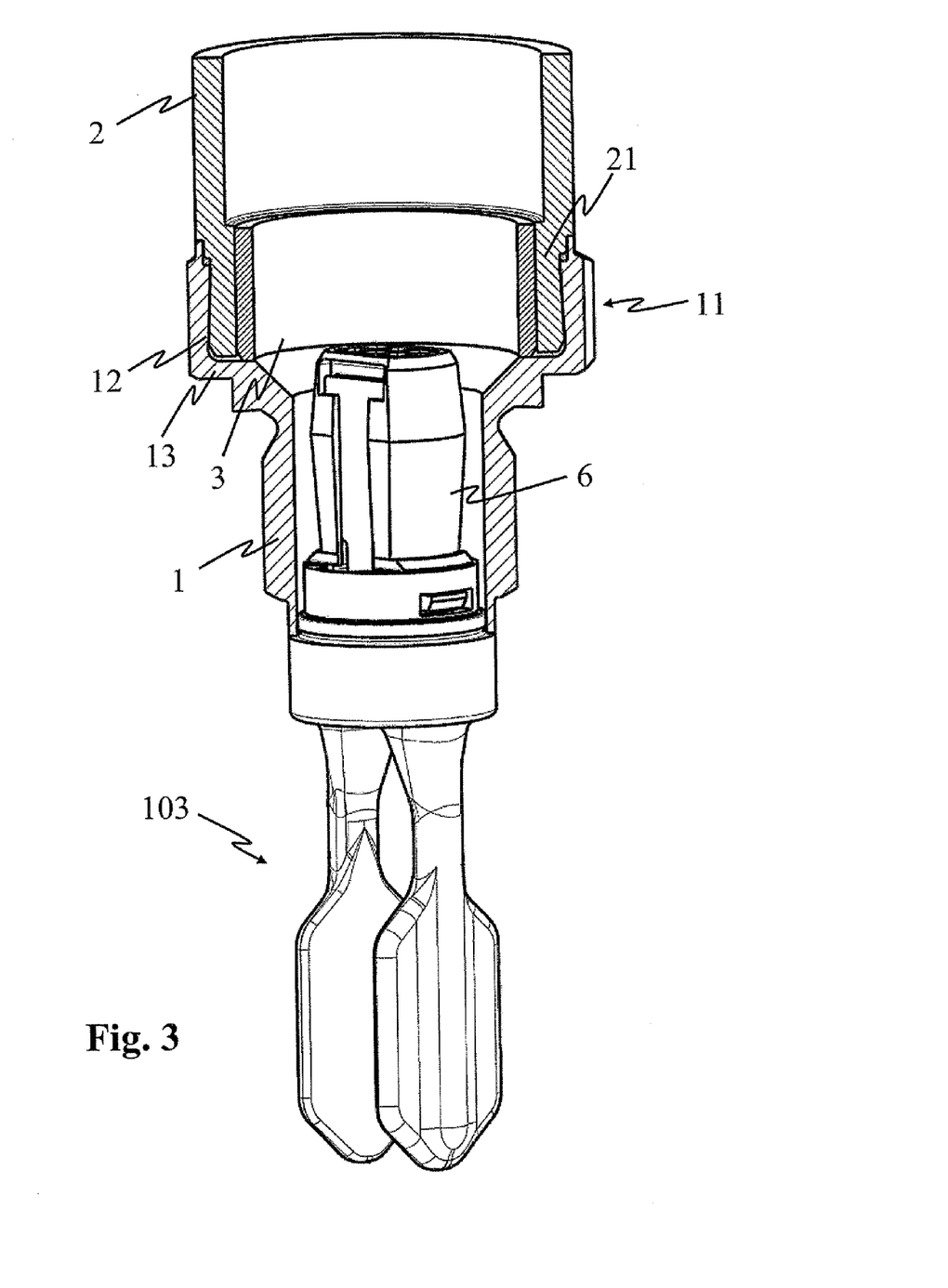
FIG. 3 is a second form of embodiment of the joint between process connection and housing.

FIG. 3 shows a second form of embodiment of the connection region between the first component 1 and second component 2. The first component 1 and the first connection region 11 are essentially embodied as in the form of embodiment illustrated in FIG. 2, except as regards the shape of the cavity 12. The cavity 12 is here embodied in such a manner that the inner diameter of the first connection region 11 steadily increases over the entire height of the first connection region 11 in the direction of the shoulder 13. The wall thickness of the first connection region 11 lessens correspondingly steadily toward the shoulder 13. The cavity is produced as an indentation via a conical chamfer.

The second connection region 21 is embodied as a corresponding counterpart for the cavity 12. As in FIG. 2, the second connection region 22 is essentially ring-shaped and arranged in such a manner in the first connection region 11 that an air gap still exists between the second connection region 22 and the shoulder 13. Instead of detents 22, the second connection region 21 has a downwards—i.e. in the direction of shoulder 13—steadily growing wall thickness. The outside of the second connection region 22 extends parallel to the wall of the cylindrical section of the second component 2, while the inner side is inclined due to the non-uniform thickness. Without the securement means 3, the second connection region still does not engage in the cavity 12. The securement means 3, however, presses the second connection region 22 in such a manner against the first connection region 11 that a force- and shape interlocking connection arises. For producing the spring action, the second connection region 21 is preferably likewise divided by slots into a number of tongues.

For locking the securement means 3 in the axial direction, the variants explained in connection with the illustrations of FIG. 2, respectively FIGS. 2a and 2b, are analogously applicable.

LIST OF REFERENCE CHARACTERS

1 first component
11 first connection region
12 cavity
13 shoulder
2 second component
21 second connection region
22 detent
23 locking element
24 groove
3 securement means
4 sealing ring
5 retaining ring
6 connection plug
100 measuring device
101 process connection
102 housing
103 sensor element
104 container
105 medium

The invention claimed is:

1. An apparatus for determining and/or monitoring at least one process variable of a medium in a container or a pipeline, comprising:
at least one sensor element sensitive for the process variable;
a process connection for securing the apparatus to the container or pipeline; and
a housing for residing outside of the container or pipeline, which housing is connected with the said process connection, wherein:
the apparatus has at least one, first component of metal and at least one, second component of synthetic material, said first component and said second component are embodied as hollow bodies;
an essentially annular, first connection region is formed on said first component;
on said second component an essentially annular, second connection region is formed;
at least a section of said second connection region has an outer diameter that corresponds essentially to the inner diameter of said first connection region;
said second connection region is introduced into said first connection region; and
a securement means is present, which is dimensioned and positioned in such a manner that the securement means presses at least a section of said second connection region against said first connection region; and
said second component has agroove and a retaining ring is introduced into said groove to affix said securement means in the axial direction.

2. The apparatus as claimed in claim 1, wherein:
said first connection region has at least one cavity.

3. The apparatus as claimed in claim 2, wherein:
said second connection region has at least one detent, which engages in said cavity.

4. The apparatus as claimed in claim 2, wherein:
the shape of said second connection region is matched in such a manner to said cavity that said second connection region, pressed by said securement means into said cavity, and said first connection region enter into a shape interlocking connection.

5. The apparatus as claimed in claim 1, wherein:
said first component is the process connection and said second component is the housing or a part of the housing, or said first component is a first part of said housing and said second component is a second part of said housing.

6. The apparatus as claimed in claim 1, wherein:
said securement means comprises at least a section whose contour is matched to said second component.

7. The apparatus as claimed in claim 1, wherein:
said securement means and/or said second component have/has at least one locking element, which affixes said securement means in the axial direction.

8. The apparatus as claimed in claim 1, wherein:
at least one sealing means is provided between said first connection region and said second connection region.

9. The apparatus as claimed in claim 1, wherein.
said first component and said second component have essentially the same outer diameter, at least in a connecting section between said first component and said second component.

* * * * *